United States Patent [19]

Firestone et al.

[11] 4,447,602

[45] May 8, 1984

[54] PROCESS TO PREPARE 7-SUBSTITUTED CEPHALOSPORINS OR 6-SUBSTITUTED PENICILLINS

[75] Inventors: Raymond A. Firestone, Fanwood; Lovji D. Cama, Edison; Burton G. Christensen, Scotch Plains, all of N.J.

[73] Assignee: Merck & Co., Inc., Rahway, N.J.

[21] Appl. No.: 803,332

[22] Filed: Jun. 3, 1977

Related U.S. Application Data

[63] Continuation of Ser. No. 647,252, Jan. 7, 1976, abandoned, which is a continuation-in-part of Ser. No. 340,803, Mar. 13, 1973, abandoned, which is a continuation-in-part of Ser. No. 203,056, Nov. 29, 1971, abandoned.

[51] Int. Cl.$^3$ .................. C07D 501/04; C07D 499/04
[52] U.S. Cl. ..................................... 544/21; 260/239.1; 544/15; 544/16; 544/22; 544/24; 544/25; 544/26; 544/27; 544/28; 544/29; 544/30
[58] Field of Search ...................... 260/239.1, 306.7 C; 544/21, 15, 22, 24, 26, 28, 29, 30, 16, 25, 27

[56] References Cited

U.S. PATENT DOCUMENTS 3,994,885 11/1976 Koppel ........................... 260/243 C
4,044,000  8/1977 Koppel ........................... 260/239.1

FOREIGN PATENT DOCUMENTS 7242357 11/1973 France ............................. 260/239.1

*Primary Examiner*—Natalie Trousof
*Assistant Examiner*—Vera C. Clarke
*Attorney, Agent, or Firm*—Raymond M. Speer; Hesna J. Pfeiffer

[57] ABSTRACT

A process is provided which yields derivatives of cephalosporins and penicillins. The process starts with 7-acylaminocephalosporin, or 6-acylaminopenicillin, then the latter compounds are treated with an organolithium compound, followed with t-butyl-hypochlorite. Finally, a defined reagent is added yielding a side chain on the carbon adjacent to the amino-nitrogen. Novel intermediate compounds are also described. The end compounds prepared are active against both gram-positive and gram-negative bacteria.

20 Claims, No Drawings

PROCESS TO PREPARE 7-SUBSTITUTED CEPHALOSPORINS OR 6-SUBSTITUTED PENICILLINS

RELATIONSHIP TO OTHER APPLICATIONS

This is a continuation of application Ser. No. 647,252, filed Jan. 7, 1976, now abandoned, which in turn is a continuation-in-part application of copending U.S. Ser. No. 340,803, filed Mar. 13, 1973, now abandoned, which in turn is a continuation-in-part application of U.S. Ser. No. 203,056, filed Nov. 29, 1971, now abandoned.

This invention relates to a new process for preparing compounds known chemically as 7-acylaminocephalosporanic acid derivatives having substituents at position 7. This process is also useful in preparing the analogous 6-substituted compounds in the penicillin series.

The compounds prepared by the process of this invention are the following—(the numbers indicate ring position):

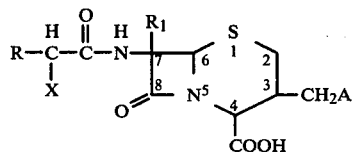

and

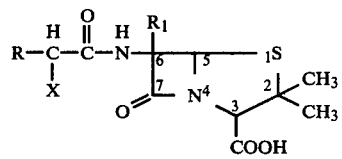

wherein $R_1$ is loweralkoxy, loweralkanoyloxy, cyano, or hydroxy;

X is hydrogen, amino, or carboxyl; R is phenyl or a 5-membered heterocyclic ring having 1–2 hetero atoms, the latter being either S, O, or N; A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; and M is sodium, potassium, benzyl, benzhydryl, trimethylsilyl, trichloroethyl, methoxymethyl, hydrogen, benzoylmethyl, or methoxybenzyl.

By the phrase "5-membered heterocyclic ring having 1–2 heteroatoms, the latter being either S, O, or N" is meant any of those 5-membered cyclic organic structures, saturated or unsaturated, which have sulfur, oxygen, or nitrogen in 1 or 2 positions in the ring. It is meant to include within this definition, mono- or di-aza, mono- or di-oxa, or mono- or di-thio ring structures, as well as rings having mixed hetero atoms. Hetero rings which are included within this definition are isoxazole, oxazole, isothiazole, thiazole, pyrazole, 3H-pyrazole, 4H-pyrazole, imidazole, 2H-imidazole, 4H-imidazole, 3H-1,2-oxathiole, 1,2-oxathiolane, 5H-1,2-oxathiole, 1,3-oxathiole, 1,2-dioxole, 1,3-dioxole, 1,3-dioxolane, 3H-1,2-dithiole, 1,2-dithiolane, 1,3-dithiole, 1,3-dithiolane, pyrrole, pyrroline, pyrrolidine, 2H-pyrrole, 3H-pyrrole, furan, or tetrahydrofuran, etc. It is understood that the point of attachment of these rings to the rest of the molecule can be in any suitable position of the ring.

It is noted that when X is amino or carboxyl, it can be blocked for protection during the series of reactions described herein, then the blocking group removed subsequently as desired.

The nomenclature used in this application is further defined as follows: The compound,

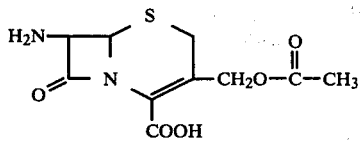

is called 7-aminocephalosporanic acid. The side chain at 3 is inherently contained in the name. By comparison, the skeleton

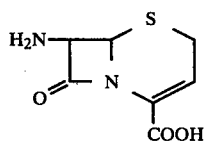

is called 7-aminodecephalosporanic acid. Derivatives of this compound which have substituents at 3- are named 7-amino-3-R-decephalosporanic acid.

In the above structural formulas, Compound I is 7-acylamino-7-$R_1$-3-$CH_2$A-decephalosporanic acid, and Compound II is a 6-acylamino-6-$R_1$-penicillanic acid.

In summary, this invention provides a route for substituting the desired $R_1$ group at position 7- (or 6-) of the desired cephalosporin (or penicillin).

The starting materials useful in this process are the following:

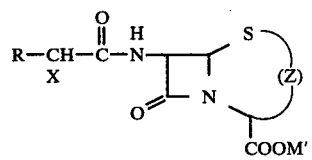

wherein R, and X are as defined above, and M' is benzyl, benzhydryl, trimethylsilyl, trichloroethyl, methoxymethyl, benzoylmethyl, or methoxybenzyl, and "—Z—" is used in Formula III to represent either the group

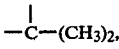

or the group

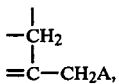

respectively, representing the penicillin or the cephalosporin structures. A is as defined above. The use of Z is appropriate since any of a great number of substituents can depend from that part of the ring, in both the penicillin and the cephalosporin series. The inventive process of this invention, involving as it does the carbon adjacent to the amino group, is not affected by the substituent at Z. One can readily see that the exemplary substituents of this application are illustrative only of preferred embodiments and that many other substituents can be employed.

These starting materials are prepared by acylating the desired cephalosporin or penicillin having a free 7- (or 6-) amino group. The acylating agent is a substituted acetic acid halide or anhydride; most suitably a substituted acetic acid chloride having the formula:

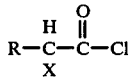
                                                    IV

The free amino-containing compound and the acylating agent are mixed together in approximately equimolar amounts in an inert solvent. The reaction proceeds spontaneously and quickly, being completed within a few hours. The 7-acylaminocephalosporin or 6-acylaminopenicillin (III) is then recovered and purified using standard procedures.

The starting material III is then treated in a sequence of reactions to yield an acyl imine intermediate. The sequence of reactions are described as preferably occurring in one reaction vessel; however, it may be desirable to isolate or conduct the reaction in different vessels; this modification is deemed within the skill of the practitioner.

Preferably, the starting material is first dissolved in an inert solvent. Any solvent which does not hinder the further reactions is practical, common operable solvents including methylene chloride or tetrahydrofuran. However, the presence of the solvent or its identity is not critical to the reaction.

The starting material is then cooled to a low temperature. This is a critical step in the reaction. Preferably, the temperature to which it is cooled is below −60° C.; most preferably, it is between −100° C. and −50° C. It is also useful to introduce an inert atmosphere to the reaction vessel at this point to minimize undesirable side reactions; nitrogen or one of the inert gases, such as argon, helium, etc., would be suitable.

Once the starting material is at the low temperature, it is admixed with about an equivalent of an organolithium compound which had previously also been brought to the low temperature. The identity of the organolithium compound is not critical, although, as it will be apparent, certain organolithiums are more desirable to increase yield and minimize side reactions. Specifically, aryllithiums, such as phenyllithium or tolyllithium or other substituted phenyllithiums can be used. Alkyllithiums, wherein alkyl can be straight or branched having 1–6 carbon atoms, are also useful, such as methyllithium or t-butyllithium. Lithium alkylamides or dialkylamides wherein alkyl is either straight or branched having 1–6 carbon atoms, e.g., lithium diisopropylamide, are also useful.

The organolithium is either added to the starting material or vice versa. The organolithium, particularly the lithiumamides, can also be prepared in situ, i.e., by dissolving, e.g., methyllithium, then adding, e.g., diisopropylamine, stirring, and adding the starting material.

It will be clear from the above discussion that about a stoichiometric or equivalent amount of some organic lithium base is necessary. The exact chemical identity of the organolithium is not critical.

As has been stated, the temperature of both the starting material and the organolithium are below −20° C. preferably −100° C. to −50° C. The addition of the two is completed within a relatively short period of time. Following the addition, while the temperature is kept within the desirable temperature range, an excess, and preferably from about 1–3 equivalents, of an active halogen transfer agent is added. Preferably, an active chlorine or bromine transfer agent is used, but the other halogens are operable. By the term "an active halogen transfer agent" is meant a chemical compound having a halogen attached to a carbon or hetero atom of the chemical compound and having electrochemical bond strengths within the compound such that the hetero atom portion of the compound can easily form an anion. Besides a hetero atom, a carbon atom fragment can also serve as the anion portion, if it has anion stabilizer groups attached. Examples of such compounds can be readily supplied by those skilled in the art; for instance, commonly used compounds include N-chloroacetamide, N-bromoacetamide, N-chlorosuccinimide, N-bromosuccinimide, t-butyl hypobromite, t-butyl hypochlorite, N-chlorosulfonamide, N-bromosulfonamide, α-chloromalonic esters and various derivatives of these compounds, such as N-chloro(substituted)sulfonamides, etc.

The halogen transfer agent is preferably lowered in temperature to the reaction range before addition.

Following addition of the halogen transfer agent, there is an optional "rest period" for the reaction. The mixture is permitted to rest for 1–15 minutes, and then optionally brought to a warmer temperature, from about −30° C. to 0° C., preferably −20° C. to −10° C. Although we prefer to conduct the next step at the higher temperature, it is not essential; the entire reaction can be conducted below −40° C.

The purpose for the "rest period", although it is not critical to the reaction, is to allow the various components in the reaction mixture to react to yield the desired intermediate acylimine compound:

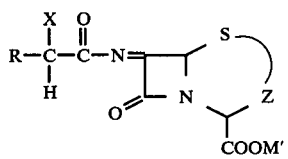
                                                    V wherein R, X, M′, and Z are as defined.

Although we are not completely sure of the mechanics of this reaction and do not with to be bound by theory, it appears that generally a reactant is formed is situ during the reaction which can be termed a "strong hindered base". By this phrase is meant a strong base which can react with the halogen supplied by the halogen transfer agent but which will not subsequently participate in any undesirable side-reactions, especially with the relatively fragile β-lactam ring. For example, when the halogen transfer agent is t-butyl hypochlorite, the strong hindered base formed is lithium t-butoxide. In turn, this ultimately yields lithium chloride and t-butanol. The latter does not react with the β-lactam since the alcohol is strongly hindered by the three methyl groups around it.

Obviously, the identity of the "strong hindered base" depends upon the identity of the halogen transfer agent. We have found that in any case it is desirable to add about an additional equivalent of lithium t-butoxide or a similar hindered base in addition to that formed in situ. For example, suitable hindered bases include diazabisbicyclononane (DBN), diazabicycloundecane (DBU), di-t-butyl-potassium-phenoxide, 1,8-bis(dimethylamino)naphthalene, N-lithiosuccinimide, etc. The additional amount of the hindered base is added before the mixture is warmed to the higher temperature range, i.e., −30° C. and above.

Once the reaction mixture is at the higher temperature range, all reactants having been added, the reagent capable of adding onto the desired 7α(or 6α) position of the cephalosporin or penicillin is added. The specific choice of reagent depends upon the desired group at position 7- (or 6-) of the cephalosporin or penicillin. Methanol is employed when a methoxy group is desired; water is used to prepare a hydroxy substituent; and hydrogen cyanide is used to prepare a cyano substituent. Obviously, the loweralkoxy or loweralkanoyloxy groups can be prepared using the lower alkanol or lower alkanoic acids as reagents. Other useful reagents include hydrazoic acid, to yield an azido group; hydrogen sulfide, to yield a mercapto group; any hydrohalic acid, such as hydrogen chloride, hydrogen fluoride, or hydrogen bromide, to yield the chloro, fluoro, or bromo groups, respectively; or a lower alkylmercaptan, such as methyl mercaptan, to yield loweralkylthio, especially methylthio.

These reagents can all be described by the formula $$R_1H \qquad VI$$

wherein $R_1$ is hydroxy, mercapto, formyloxy, loweralkanoyloxy, lower alkoxy, loweralkylthio, azido, fluoro, chloro, bromo, or cyano.

Besides the reagents being employed as the free acids, they can also be used as anions in a tertiary amine salt. Suitable tertiary amine cations include triloweralkyl ammonium, wherein alkyl can be the same or different and has 1-6 carbon atoms, such as triethylammonium, and pyridinium. As typical examples of useful salts, are included: triethylammonium formate, pyridinium sulfide, triethylammonium chloride, and the like. The tertiary amine salts can be easily prepared and used in the reaction as described below.

The chosen reagent is employed in approximately equimolecular amounts, although a molecular excess can be used successfully. The mixture is then permitted to react, while stirring if desired, for from 5–60 minutes, and the temperature allowed to rise to ambient temperature. The reaction is then quenched by the addition of a solvent such as benzene, which contains a small amount of acetic acid. The solution is then washed and worked up using conventional procedures to recover the desired end products I or II.

The compounds prepared by the process of this invention are useful as antibacterial agents against both gram-positive and gram-negative bacteria. In addition, resistance to β-lactamases has been demonstrated. The activity spectrum includes effectiveness against many bacteria, including in vivo on *Proteus morganii*, and, in addition, against *E. coli*, *P. vulgaris*, *P. mirabilis*, *S. schottmuelleri*, *K. pneumoniae AD*, *K. pneumoniae B*, and *P. arizoniae*.

In addition to the specific end product as defined in structural formula I, other compounds which are active antibacterials can also be prepared using the process described herein. The compounds which can be prepared have the following structural formula:

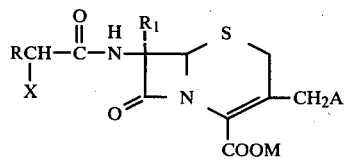

It is noted that the analogous $\Delta^2$ compounds which can also be prepared using the processes described herein are valuable intermediate compounds because of their greater acid stability, and can be converted to $\Delta^3$ compounds easily. The various substituents have the following meanings: X is halogen, halo, amino, guanidino, phosphono, hydroxy, tetrazolyl, carboxyl, sulfo, or sulfamino;

R is phenyl, substituted phenyl, a monocyclic heterocyclic 5- or 6-membered ring containing one or more oxygen, sulfur, or nitrogen atoms in the ring, substituted heterocyclics, phenylthio, heterocyclic, or substituted heterocyclic thio-groups, or cyano; the substituents on the R group being halo, carboxymethyl, guanidino, guanidinomethyl, carboxamidomethyl, aminomethyl, nitro, methoxy, or methyl;

A is hydrogen, hydroxy, halo, mercapto, cyano, alkanoyloxy, alkanoylthio, aroyloxy, aroylthio, heteroaryloxy or heteroarylthio, the hetero ring having 5–6 members and having 1–3 hetero atoms, being O, S, or N or combinations thereof, azido, amino, carbamoyloxy, alkoxy, alkylthio, carbamoylthio, thiocarbamoyloxy, benzoyloxy, (p-chlorobenzoyl)oxy, (p-methylbenzoyl)oxy, pivaloyloxy, (1-adamantyl)carboxy, substituted amino such as alkylamino, dialkylamino, alkanoylamino, carbamoylamino, N-(2-chloroethylamino), 5-cyano-triazol-1-yl, 4-methoxycarbonyl-triazol-1-yl, or quaternary ammonium such as pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium, or lutidinium; N-loweralkylcarbamoyloxy, N,N-diloweralkylthiocarbamoyloxy, alkanoylcarbamoyloxy, hydroxyphenyl, sulfamoyloxy, alkylsulfonyloxy, or (cis-1,2-epoxypropyl)phosphono;

and M is an alkali metal, benzyl, alkanoyloxymethyl, alkylsilyl, phenalkanoyl, benzhydryl, alkoxyalkyl, alkenyl, trichloroethyl, hydrogen, benzoylmethyl, or methoxybenzyl.

Preferably in the compounds of Formula V, X is hydrogen, amino or carboxyl, R is phenyl, or a 5–6 membered heterocyclic ring having 1–2 hetero atoms, the latter being either S, O, or N;

A is hydrogen, halo, azido, cyano, hydroxy, alkoxy, carbamoyloxy, thiocarbamoyloxy, N-loweralkylcarbamoyloxy, N,N-diloweralkylcarbamoyloxy, N-loweralkylthiocarbamoyloxy, N,N-diloweralkylthiocarbamoyloxy, alkanoyloxy, aroyloxy, mercapto, alkylthio, amino, alkylamino, alkanoylamino, hydroxyphenyl, sulfamoyloxy, quaternary ammonium, alkylsulfonyloxy, or (cis-1,2-epoxypropyl)phosphono;

and M is alkali metal, benzyl, alkylsilyl, phenalkanoyl, alkoxyalkyl, pivaloyloxymethyl, alkenyl, trichloroethyl, hydrogen, benzoylmethyl, or methoxybenzyl.

Even more preferably, X is hydrogen, amino, or carboxyl; R is phenyl or a 5-membered heterocyclic ring having 1-2 hetero atoms, the latter being either S, O, or N;

A is hydrogen, loweralkanoyloxy, heteroarylthio, carbamoyloxy, thiocarbamoyloxy, N-loweralkylcarbamoyloxy, N-loweralkylthiocarbamoyloxy, N,N-diloweralkylthiocarbamoyloxy, pyridinium, alkylpyridinium, halopyridinium, or aminopyridinium; and M is sodium, potassium, benzyl, benzhydryl, trimethylsilyl, trichloroethyl, methoxymethyl, hydrogen, benzoylmethyl, or methoxybenzyl.

Still more preferably, X is hydrogen or carboxyl;
R is phenyl, or a 5-membered heterocyclic ring having one O or one S hetero atom;
A is hydrogen, loweralkanoyloxy, carbamoyloxy, N-loweralkylcarbamoyloxy, N,N-diloweralkylcarbamoyloxy, pyridinium, alkylpyridinium, halopyridinium, or aminopyridinium;
And M is sodium, potassium, benzhydryl, methoxymethyl or hydrogen.

Most preferably, X is hydrogen or carboxyl;
R is phenyl, thienyl, or furyl;
A is hydrogen, loweralkanoyloxy, carbamoyloxy, or pyridinium; and
M is sodium, potassium, benzhydryl, methoxymethyl, or hydrogen.

In addition, compounds of Formula VII above wherein the sulfur atom is present as the sulfoxide

can be prepared in this inventive reaction. It will also be apparent that the process described herein can also be used to prepare analogous compounds in the penicillin series:

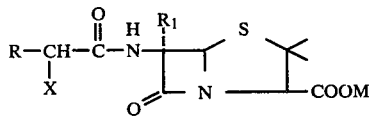

VIII wherein R, $R_1$, M, X, and A are the same as defined in Formula VII.

The compounds of Formula VII can generally be prepared from 7-ACA or known derivatives thereof using the general process outlined in the preparative examples.

The blocking group on the acid functionality at position-4 of the cephalosporin ring (or position-3 of the penicillin) can be removed following any of the reactions of this invention. The removal can be accomplished using methods available to those in the art.

The penicillins of Formula VIII can be prepared from 6-APA or known derivatives thereof using procedures analogous to those described for the cephalosporins.

Other starting materials useful in the application of these inventive reactions can be prepared in accordance with known methods, see, e.g., Belgium Pat. No. 650,444 or U.S. Pat. No. 3,117,126, or using the following preparations.

The term "loweralkyl" is employed to mean a carbon chain having 1-6 carbon atoms; when more than one loweralkyl group appears in a substituent, the groups can be the same of different. "Lower alkanoyl" means having 1-6 carbon atoms.

PREPARATION 1

3-Hydroxymethyl-7-Aminodecephalosporanic Acid

The 3-hydroxymethyl-7-aminodecephalosporanic acid is obtained as the lactone by acid hydrolysis of cephalosporin C in accordance with procedures known in this art.

PREPARATION 2

3-Pyridiniummethyl-7-Aminodecephalosporanic Acid

This compound is prepared by treating cephalosporin C with pyridine followed by acid hydrolysis as described in U.S. Pat. No. 3,117,126.

PREPARATION 3

3-Methyl-7-Aminodecephalosporanic Acid

This compound is prepared from cephalosporin C by catalytic reduction followed by hydrolytic removal of the 5-aminodipoyl side chain as described in U.S. Pat. No. 3,129,224.

PREPARATION 4

3-Chloromethyl-7-Aminodecephalosporanic Acid

This compound is prepared from the 3-methyl compound by reaction with chlorine gas. The bromomethyl or iodomethyl derivatives can be prepared from the 3-hydroxymethyl compound by reaction with phosphorus tribromide or phosphorus triiodide, respectively.

The starting materials used in the preparation of the compounds of Formula I can be prepared as follows:

PREPARATION 5

3-Carbamoyloxymethyl-7-Aminodecephalosporanic Acid

7-Aminocephalosporanic acid is treated with 5-butoxycarbonylazide to produce the 7β-(t-butoxycarbonyl) derivative in accordance with known methods. This derivative is then intimately contacted with citrus acetylesterase in aqueous phosphate buffer at pH 6.5-7 for 15 hours and 3-hydroxymethyl 7β-(t-butoxycarbonyl)aminodecephalosporanic acid is recovered from the resulting reaction mixture.

To 0.2 g. of 3-hydroxymethyl 7β-(t-butoxycarbonyl)aminodecephalosporanic acid suspended in 5 ml. of acetonitrile, cooled to 0° C., and maintained under nitrogen atmosphere is added 0.15 ml. of chlorosulfonyl isocyanate. The reaction mixture is stirred for 70 minutes and then evaporated under diminished pressure to dryness. The resulting residue is taken up in 10 ml. of ethylacetate and 10 ml. of 0.1 N phosphate buffer. The pH of the aqueous layer is adjusted to about 1.6 and the mixture stirred for 2½ hours at room temperature. The pH is then adjusted to about 8 with aqueous tripotassium phosphate solution, and the aqueous phase is separated. The organic phase is re-extracted with 10 ml. of phosphate buffer at pH 8. The combined aqueous phase is adjusted to pH 2.1 with hydrochloric acid and extracted twice with ethylacetate. The ethylacetate extractions are dried over sodium sulfate and evaporated under diminished pressure to afford 0.055 g. of residue. This residue is washed with ether to afford 3-carbamoyloxymethyl-7β-(t-butoxycarbonyl)aminodecephalosporanic acid which is recovered as a yellow solid.

3-Carbamoyloxymethyl-7β-(t-butoxycarbonyl)-aminodecephalosporanic acid (0.5 g.) in 3.5 ml. of anisole is stirred with 2 ml. of trifluoroacetic acid at 0° C. for 5 minutes. The resulting reaction mixture is evaporated under reduced pressure to afford 3-carbamoyloxymethyl-7-aminodecephalosporanic acid which is purified further by crystallization from ethylacetate.

PREPARATION 6

Trimethylsilyl 3-Carbamoyloxymethyl-7-Aminodecephalosporanate

A mixture of 0.5 g. of 3-carbamoyloxymethyl-7-aminodecephalosporanic acid, 2 ml. of hexamethyldisilazane and 8 ml. of chloroform is stirred overnight at reflux temperature protected from moisture. The solvent and excess hexamethyldisilazane are removed at reduced pressure, leaving a residue containing trimethylsilyl 3-carbamoyloxymethyl-7-aminodecephalosporanate.

PREPARATION 7

Benzhydryl 7-(2-Thienylacetamido)-3-Carbamoyloxymethyl-Decephalosporanate

A. 7-Amino-3-Carbamoyloxymethyldecephalosporanic Acid Benzhydryl Ester

272 Mg. of 7-amino-3-carbamoyloxymethyldecephalosporanic acid is slurried 5 minutes at 25° C. in 7 ml. of dioxane with 170 mg. of p-toluenesulfonic acid H$_2$O. Methanol (2 ml.) is added, the solvents are removed in vacuo, and dioxane is twice added and evaporated in vacuo. Dioxane (8 ml.) is added, and then 290 mg. of diphenyldiazomethane. After the evolution of nitrogen is complete, the solvent is distilled in vacuum, and the residue stirred with methylene chloride (10 ml.) and water (10 ml.) containing sufficient K$_2$HPO$_4$ to bring the pH to 8. The layers are separated and the aqueous portion extracted twice more with CH$_2$Cl$_2$. The combined organic layers are dried with sodium sulfate, filtered and evaporated, leaving oily crystals. Washing with ether affords a dry solid, 150 mg. (35%), m.p. 110°–115° C. which is the product, 7-amino-3-carbamoyloxymethyldecephalosporanic acid benzhydryl ester.

In a like manner, the benzhydryl and other esters of 3-methyl-7-aminodecephalosporanic acid, 3-chloromethyl-7-aminodecephalosporanic acid, and 7-aminocephalosporanic acid can be prepared.

B. Benzhydryl 3-Carbamoyloxymethyl-7-(2-Thienylacetamido)-Decephalosporanate

Benzhydryl 7-amino-3-carbamoyloxymethyldecephalosporanate (452 mg.) is reacted with 161 mg. of thienyl acetyl chloride in 25 ml. of methylene chloride containing 0.5 ml. of pyridine.

The reaction mixture is held at 0° C. for 15–60 minutes and then raised to room temperature and held an additional 15–60 minutes. The mixture is then washed with water, dilute phosphoric acid (buffered to pH 2), water, and dilute sodium bicarbonate. After drying over MgSO$_4$, the solution is filtered and evaporated. The crude solid is purified by chromatography on silica gel and eluted using for instnace, 4:1 chloroform:ethyl acetate. The product prepared is the benzhydryl 7-(2-thienylacetamido)-3-carbamoyloxymethyldecephalosporanate.

PREPARATION 8

Benzyl 6-(2-Phenylacetamido)-Penicillanate

The benzyl ester of 6-APA is reacted with 2-phenyl acetyl chloride using the same reaction conditions as described above. The product, benzyl 6-(2-phenylacetamido)-penicillanate is recovered and identified.

EXAMPLE 1

Benzyl 6α-Methoxy-6β-(2-Phenylacetamido)-Penicillanate

Benzyl 6-(2-phenylacetamido)-penicillanate (0.25 mmole) in 5 ml. of tetrahydrofuran is cooled to −78° C. under nitrogen. One equivalent (0.109 ml. of 2.3 M) phenyl lithium is added followed by 35 microliters of t-butyl hypochlorite. This mixture is permitted to stand 60 seconds while the temperature is raised to −17° C., then one ml. methanol is added to the solution. The mixture is removed from the ice bath and stirred for 5 minutes, then 40 ml. benzene containing 0.1 ml. acetic acid is added. The solution is washed with water containing pH 2 phosphate buffer; water, and finally water containing pH 8 phosphate buffer; dried with MgSO$_4$, filtered and evaporated to afford 87 mg. crude benzyl 6α-methoxy-6β-(2-phenylacetamido)-penicillanate. The pure compound, 13 mg., is obtained after purification by chromatography on 5 g. silica gel, eluting with 4:1 chloroform/ethyl acetate.

EXAMPLE 2

Benzyl 6α-Hydroxy-6β-(2-Phenylacetamido)-Penicillanate

Benzyl 6β-(2-phenylacetamido)penicillanate, 0.106 g. (0.25 mmole), in 5 ml. THF is cooled to −78° C. under nitrogen. One equivalent (0.109 ml. of 2.3 M) phenyllithium is added, followed by 0.060 ml. t-butyl hypochlorite. After 1 minute at −78° C., a solution of 0.024 ml. of t-butyl alcohol and 0.109 ml. 2.3 M phenyllithium in 2 ml. THF is added. The reaction mixture is warmed to −17° C., forming the imino intermediate compound in situ.

To this solution is added 0.1 ml. water in 2 ml. THF at −17° C. The reaction is stirred 5 minutes out of the ice bath, and then 40 ml. of benzene containing 0.1 ml. acetic acid is added. The solution is washed with water containing pH 2 phosphate buffer, water, and finally water containing pH 8 phosphate buffer; dried with MgSO$_4$; filtered and evaporated, affording the crude product. Chromatography on silica gel, eluting with 4:1 CHCl$_3$-EtoAc, affords pure benzyl 6α-hydroxy-6β-(2-phenylacetamido)penicillanate, 25 mg.

EXAMPLE 3

Benzyl 6α-Cyano-6β-(2-phenylacetamido)Penicillanate

Benzyl 6β-(2-phenylacetamido)penicillanate, 0.106 g., in 5 ml. of tetrahydrofuran is cooled to −78° C. under nitrogen. Phenyllithium, 0.109 ml. of 2.3 M, is added, followed by 0.060 ml. t-butyl hypochlorite. After 1 minute is added a solution of 0.2 ml. hydrogen cyanide and 0.164 ml. of phenyllithium in 2 ml. of tetrahydrofuran. The reaction is allowed to warm to room temperature over 20 minutes, and then worked up as in Example 2 above. Chromatography affords a small amount of benzyl 6α-cyano-6β-(2-phenylacetamido)-penicillanate, identified by mass spectroscopy.

EXAMPLE 4

Benzyl 6β-(2-Phenylacetamido)-6α-Formyloxypenicillanate

Using the same general process described above in Example 2, a solution of the imino intermediate at −17° C. is treated with 0.075 ml. of anhydrous formic acid and 0.278 ml. of triethylamine in 4 ml. of tetrahydrofuran. After 5 minutes stirring out of ice, 40 ml. of benzene is added, and the reaction mixture washed twice with water. The mixture is purified as above, yielding 9 mg. of benzyl-6β-(2-phenylacetamido)-6α-formyloxypenicillanate.

In the same manner, benzyl 6β-(2-phenylacetamido)-6α-azidopenicillanate, benzyl 6β-(2-phenylacetamido)-6α-chloropenicillanate, benzyl 6β-(2-phenylacetamido)-6α-bromopenicillanate, benzyl 6β-(2-phenylacetamido-6α-mercaptopenicillanate, or benzyl 6β-(2-phenylacetamido)-6α-methylthiopenicillanate is prepared respectively, using hydrazoic acid, hydrochloric acid, hydrobromic acid, hydrogen sulfide, or methylmercaptan.

EXAMPLE 5

Benzhydryl 7β-(2-Thienylacetamido)-7α-Methoxy-3-Carbamoyloxymethyldecephalosporanate Using the same process as described in Example 1, using benzhydryl 7β-(2-thienylacetamido)-3-carbamoyloxymethyldecephalosporanate as the starting material, the product benzhydryl 7β-(2-thienylacetamido)-7α-methoxy-3-carbamoyloxymethyldecephalosporanate is prepared. The other cephalosporin derivatives can also be prepared using processes described in Examples 2–4.

EXAMPLE 6

3-Carbamoyloxymethyl-7-Methoxy-7-(2-Thienylacetamido)-Decephalosporanic Acid

Benzhydryl 3-carbamoyloxymethyl-7-methoxy-7-(2-thienylacetamido)decephalosporanate (300 mg.) in 0.5 ml. in anisole and 2.5 ml. of trifluoroacetic acid is reacted for 15 minutes at 10° C. The resulting mixture is evaporated at reduced pressure and flushed twice with anisole. The residue is dissolved in methylene chloride and extracted with 5% sodium bicarbonate solution. The aqueous solution is adjusted to pH 1.8 with 5% phosphoric acid and extracted with ethyl acetate. The organic solution is dried and evaporated to yield the pure 3-carbamoyloxymethyl-7-methoxy-7-(2-thienylacetamido)decephalosporanic acid, m.p. 165°–167° C. UV and NMR analysis provide data consistent with the assigned structure. The benzyl blocking group in the penicillanates can be removed in the usual manner by reduction over palladium catalyst.

EXAMPLE 7

Sodium 3-Carbamoyloxymethyl-7-Methoxy-7-(2-Thienylacetamido)-Decephalosporanate

The procedure as in Example 6 is followed, except that the pH is adjusted to 8.0 with dilute sodium hydroxide and concentrated under vacuum to remove the solvents. The mono-sodium salt of 3-carbamoyloxymethyl-7-methoxy-7-(2-thienylacetamido)decephalosporanic acid is recovered.

What is claimed is:

1. The process of preparing the compound having the formula:

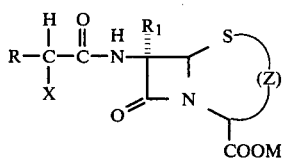

wherein
R is phenyl, thienyl or furyl;
X is hydrogen or amino;
M is sodium, potassium, benzyl, benzhydryl, trimethylsilyl, trichloroethyl, methoxymethyl, hydrogen, benzoylmethyl, or methoxybenzyl;
$R_1$ is hydroxy, mercapto, formyloxy, loweralkanoyloxy, loweralkoxy, loweralkylthio, azido, fluoro, chloro, bromo, or cyano; and
(Z) is the group

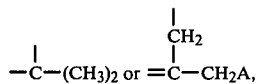

wherein A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; which comprises reacting the compound having the formula:

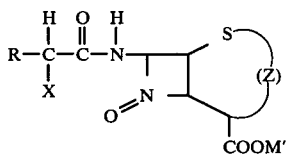

wherein R, X, and Z are as defined above, and M' is benzyl, benzhydryl, trimethylsilyl, trichloroethyl, methoxymethyl, benzoylmethyl, or methoxybenzyl;

(a) with approximately an equivalent of an organolithium compound chosen from the group consisting of phenyl lithium, tolyl lithium, alkyl lithium having 1–6 carbon atoms in the alkyl chain, or lithium alkylamide or lithium dialkylamide, alkyl having 1–6 carbon atoms in the alkyl chain at a temperature below about −20° C.

(b) then adding from about 1–3 equivalents of an active halogen transfer agent chosen from the group consisting of N-chloroacetamide, N-bromoacetamide, N-chlorosuccinimide, N-bromosuccinimide, t-butylhypochlorite, N-chlorosulfonamide, or α-chloromalonic ester;

(c) then either at said temperature below −20° C. or optionally after allowing the temperature to rise up to about 0° C.;

(d) adding about an equivalent of a hindered base lithium t-butoxide, diazobiscyclononane, diazobiscycloundecane, di-t-butyl-potassium phenoxide, 1,8-bis(dimethylamino)naphthalene or N-lithiosuccinimide;

(e) adding about an equivalent amount of the reagent $R_1Q$, wherein $R_1$ is as defined above and Q is either hydrogen, triloweralkylammonium, or pyridinium, to yield the respective $R_1$ substituent, and recovering the desired product.

2. The process of claim 1 wherein X is hydrogen, $R_1$ is methoxy, and R is phenyl or thienyl.

3. The process of claim 2 wherein A is loweralkanoyloxy, carbamoyloxy, or pyridinium.

4. The process of claim 3 wherein A is acetoxy or carbamoyloxy.

5. The process of preparing the compounds having the formula:

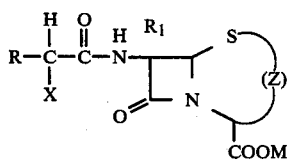

wherein

R is phenyl, thienyl or furyl;

X is hydrogen, or amino;

M is sodium, potassium, benzyl, benzhydryl, trimethylsilyl, trichloroethyl, methoxymethyl, hydrogen, benzoylmethyl, or methoxybenzyl;

$R_1$ is hydrogen, mercapto, formyloxy, loweralkanoyloxy, loweralkoxy, loweralkylthio, azido, fluoro, chloro, bromo, or cyano; and (Z) is the group

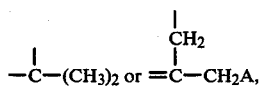

wherein A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; which comprises reacting a compound having the formula:

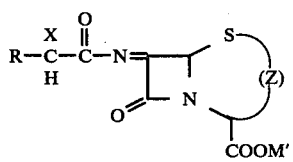

where R, X and Z are as defined above, and M' is benzyl, benzhydryl, trimethylsilyl, trichloroethyl, methoxymethyl, benzoylmethyl, or methoxybenzyl;

with approximately an equivalent amount of the reagent $R_1Q$ wherein $R_1$ is as defined above and Q is either hydrogen, triloweralkylammonium, or pyridinium, at a temperature below about 0° C., to yield the desired $R_1$ substituent, and recovering the desired product, optionally removing the deblocking group M' then treating with alkali metal base when M is sodium or potassium.

6. The process of claim 5 wherein $R_1$ is loweralkoxy and Q is hydrogen.

7. The process of claim 6 wherein $R_1$ is methoxy.

8. The process of claim 6 wherein M' is trichloroethyl.

9. The process of claim 6 where X is hydrogen and R is thienyl, phenoxy or phenyl.

10. The process of claim 6 wherein A is acetoxy or carbamoyloxy.

11. The process of preparing the compound having the formula:

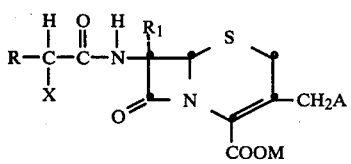

wherein

R is phenyl, thienyl or furyl;

X is hydrogen or amino;

M is sodium, potassium, benzyl, benzhydryl, trimethylsilyl, trichloroethyl, methoxymethyl, hydrogen, benzoylmethyl, or methoxybenzyl;

$R_1$ is hydroxy, mercapto, formyloxy, loweralkanoyloxy, loweralkoxy, loweralkylthio, azido, fluoro, chloro, bromo, or cyano; and wherein A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; which comprises reacting the compound having the formula:

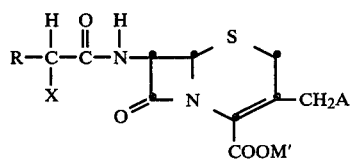

wherein R, X and A are as defined above, and M' is benzyl, benzhydryl, trimethylsilyl, trichloroethyl, methoxymethyl, benzoylmethyl, or methoxybenzyl;

(a) with approximately an equivalent of an organolithium compound chosen from the group consisting of phenyl lithium, tolyl lithium, alkyl lithium having 1–6 carbon atoms in the alkyl chain, or lithium alkylamide or lithium dialkylamide, alkyl having 1–6 carbon atoms in the alkyl chain at a temperature below about −20° C.

(b) then adding from about 1–3 equivalents of an active halogen transfer agent chosen from the group consisting of N-chloroacetamide, N-bromoacetamide, N-chlorosuccinimide, N-bromosuccinimide, t-butylhypochlorite, N-chlorosulfonamide, or α-chloromalonic ester;

(c) then either at said temperature below −20° C. or optionally after allowing the temperature to rise up to about 0° C.;

(d) adding about an equivalent of a hindered base lithium t-butoxide, diazobiscyclononane, diazobiscycloundecane, di-t-butyl-potassium phenoxide, 1,8-bis(dimethylamino)napthalene or N-lithiosuccinimide;

(e) adding about an equivalent amount of the reagent $R_1Q$, wherein $R_1$ is as defined above and $Q$ is either hydrogen, triloweralkylammonium, or pyridinium, to yield the respective $R_1$ substituent, and recovering the desired product.

12. The process of claim 11 wherein X is hydrogen, $R_1$ is methoxy, and R is phenyl or thienyl.

13. The process of claim 12 wherein A is loweralkanoyloxy, carbamoyloxy, or pyridinium.

14. The process of claim 13 wherein A is acetoxy or carbamoyloxy.

15. The process of preparing the compound having the formula

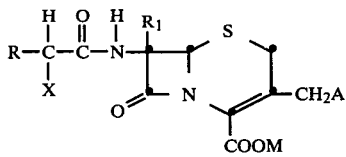

wherein
R is phenyl, thienyl, or furyl;
X is hydrogen, or amino;
M is sodium, potassium, benzyl, benzhydryl, trimethylsilyl, trichloroethyl, methoxymethyl, hydrogen, benzoylmethyl, or methoxybenzyl;
$R_1$ is hydrogen, mercapto, formyloxy, loweralkanoyloxy, loweralkoxy, loweralkylthio, azido, fluoro, chloro, bromo, or cyano; and wherein A is hydrogen, loweralkanoyloxy, carbamoyloxy, thiocarbamoyloxy, N-loweralkylcarbamoyloxy, N-loweralkylthiocarbamoyloxy, N,N-diloweralkylcarbamoyloxy, N,N-diloweralkylthiocarbamoyloxy, pyridinium, alkylpyridinium, halopyridinium, or aminopyridinium; which comprises reacting a compound having the formula:

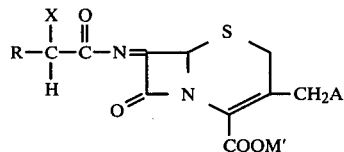

where R, X and A are as defined above, and M' is benzyl, benzhydryl, trimethylsilyl, trichloroethyl, methoxymethyl, benzoylmethyl, or methoxybenzyl;

with approximately an equivalent amount of the reagent $R_1Q$ wherein $R_1$ is as defined above and Q is either hydrogen, triloweralkylammonium, or pyridinium, at a temperature below about 0° C., to yield the desired $R_1$ substituent, and recovering the desired product, optionally removing the deblocking group M' then treating with alkali metal base when M is sodium or potassium.

16. The process of claim 15 wherein $R_1$ is loweralkoxy and Q is hydrogen.

17. The process of claim 16 wherein $R_1$ is methoxy.

18. The process of claim 16 wherein M' is trichloroethyl.

19. The process of claim 16 wherein X is hydrogen and R is thienyl, phenoxy or phenyl.

20. The process of claim 16 wherein A is acetoxy.

* * * * *